United States Patent

Duret et al.

[11] Patent Number: 6,166,035
[45] Date of Patent: Dec. 26, 2000

[54] 1,4-DIHYDROPYRIDINE DERIVATIVES AND THEIR USE IN THERAPY

[75] Inventors: Gerard Duret, Boulogne Billancourt; Gerard Glauert, Saints; Marguerite Henry, Boulogne Billancourt, all of France

[73] Assignee: Laboratoire L. Lafon, Maisons Alfort, France

[21] Appl. No.: 09/341,120

[22] PCT Filed: Jan. 12, 1998

[86] PCT No.: PCT/FR98/00042

§ 371 Date: Jul. 8, 1999

§ 102(e) Date: Jul. 8, 1999

[87] PCT Pub. No.: WO98/31680

PCT Pub. Date: Jul. 23, 1998

[30] Foreign Application Priority Data

Jan. 21, 1997 [FR] France .................................. 97 00577

[51] Int. Cl.[7] ..................... A61K 31/4545; C07D 401/12
[52] U.S. Cl. .......................... 514/318; 514/343; 546/194; 546/278.4
[58] Field of Search ................. 546/194, 278.4; 514/318, 343

[56] References Cited

U.S. PATENT DOCUMENTS 5,250,543 10/1993 Lafon et al. ............................ 514/318

FOREIGN PATENT DOCUMENTS 0 494 816 1/1992 European Pat. Off. .

*Primary Examiner*—Jane Fan
*Attorney, Agent, or Firm*—Jacobson, Price, Holman & Stern, PLLC

[57] ABSTRACT

Novel 1,4-DHP of the following structures are described having better therapeutic activities in coronary diseases:

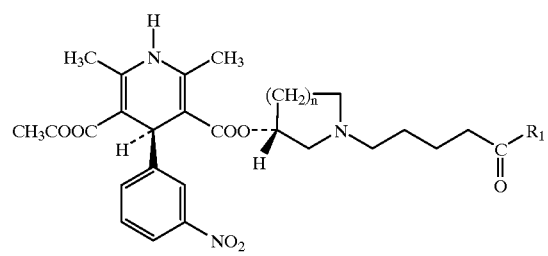

wherein n and R1 are as defined in the specification.

9 Claims, No Drawings

1,4-DIHYDROPYRIDINE DERIVATIVES AND THEIR USE IN THERAPY

This application is a 371 PCT/FR98/00042, Jan. 12, 1998 now WO 9,831,680.

The present invention relates to novel 1,4-dihydropyridine derivatives.

Various 1,4-dihydropyridine derivatives have already been described. Thus, various esters of 2,6-dimethyl-4-(3-nitrophenyl)-5-methoxycarbonyl-1,4-dihydropyridine-3-carboxylic acid and in particular the 2-[methyl (phenylmethyl)amino]ethyl ester known under the name nicardipine, have already been described, in particular in FR 2,218,107.

Other 1,4-dihydropyridine derivatives have moreover been described in EP-A-0,494,816, these derivatives containing in position 3 a chain of the type:

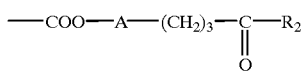

in which:

A represents a group chosen from the groups of formula:

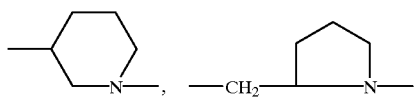

and $R_2$ represents a group chosen from 2,4,6-trimethoxyphenyl, 2-thienyl and phenyl groups.

The present invention is directed towards providing novel 1,4-dihydropyridine derivatives which have a better therapeutic range than that of compounds corresponding to the formula described in EP-A-0,494,816.

A subject of the present invention is thus compounds of formula:

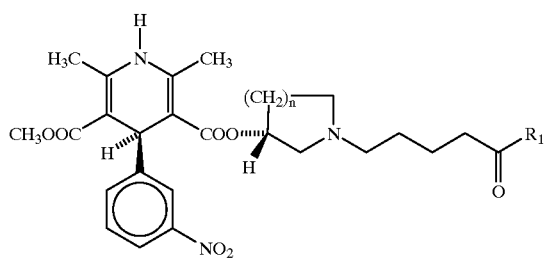

in which:
n=1 or 2, and
$R_1$ is a group selected from 2,4,6-trimethoxyphenyl, 2-thienyl and 2-pyrrolyl groups,
and the addition salts thereof with pharmaceutically acceptable acids.

The subject of the present invention is, more particularly, (4S,3'R)(−)N-[4-(2-thienoyl)butyl]-piperid-3'-yl 2,6-dimethyl-4-(3-nitrophenyl)-5-methoxycarbonyl-1,4-dihydropyridine-3-carboxylate, (4S,3'R)(−)N-[4-(2,4,6-trimethoxybenzoyl)butyl]pyrrolidin-3'-yl 2,6-dimethyl-4-(3-nitrophenyl)-5-methoxycarbonyl-1,4-dihydropyridine-3-carboxylate and (4S,3'R)(−)N-[5-(1H-2-pyrrolyl)-5-oxopentyl]piperid-3'-yl 2,6-dimethyl-4-(3-nitrophenyl)-5-methoxycarbonyl-1,4-dihydropyridine-3-carboxylate, and the addition salts thereof with pharmaceutically acceptable acids.

The expression "addition salts with pharmaceutically acceptable acids" denotes salts which give the biological properties of the free bases, without having an undesirable effect. These salts can be, in particular, those formed with inorganic acids, such as hydrochloric acid, hydrobromic acid, sulphuric acid, nitric acid or phosphoric acid; acidic metal salts, such as disodium orthophosphate and monopotassium sulphate, and organic acids.

The compounds of formula I can be obtained by reaction of the acid of formula:

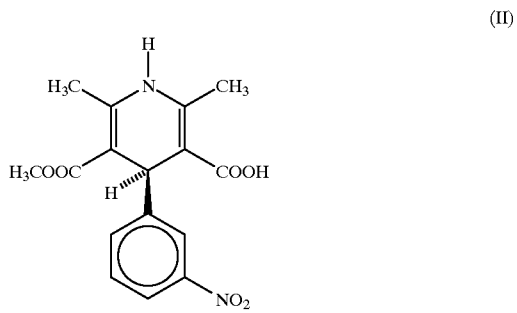

with an alcohol of formula

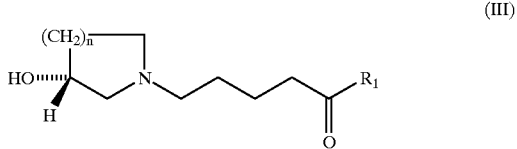

in which n and $R_1$ have the meaning given above.

The addition salts are conventionally obtained by reaction of the compound of formula I with a pharmaceutically acceptable acid in a suitable solvent. Conversely, the bases can be obtained from addition salts by treatment with a strong base.

The acid of formula II can be prepared as described in EP-A-0,494,816 or as described in EP-A-0,680,952.

The alcohols of formula III can be obtained by reaction of a compound of formula:

with a chloro derivative of formula

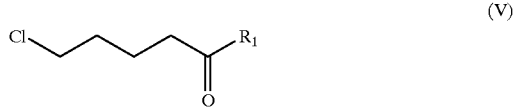

The examples which follow illustrate the preparation of the compounds according to the invention.

EXAMPLE 1

Preparation of (4S,3'R)(−)N-[4-(2-thienoyl)-butyl] piperid-3'-yl 2,6-dimethyl-4-(3-nitrophenyl)-5- methoxycarbonyl-1,4-dihydropyridine-3-carboxylate (CRL 42249)

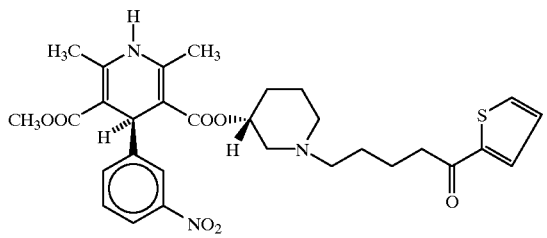

a) Preparation of 2-(5-chloropentanoyl)thiophene 16 g (0.120 mol) of aluminium chloride are introduced portionwise over 15 min into a solution, maintained at about +5°, of 20.2 g (0.240 mol) of thiophene and 15.5 g (0.100 mol) of 5-chlorovaleryl chloride and the mixture is stirred for 5 h at room temperature. After removal of the supernatant by means of separating the phases by settling, the reaction medium is taken up in 120 ml of 3N hydrochloric acid solution and extracted with chloroform.

The organic phase is washed with water and dried over dry sodium sulphate and the solvent is evaporated off to give 16.5 g of an orange-brown oil.

Yield: 81.65%.

b) Preparation of (R)-2-[5-(3-hydroxypiperidinopentanoyl]thiophene hydrochloride A solution of 20.3 g (0.10 mol) of the compound obtained in a) in 10 ml of acetonitrile is added over 45 min to a refluxing suspension of 8.1 g (0.08 mol) of (R)-3-hydroxypiperidine, prepared as described by H. Siertsson et al. (J. Med. Chem. 15, 1085, 1972), and 12.7 g (0.12 mol) of sodium carbonate in 20 ml of acetonitrile, and the mixture is maintained at reflux for 1 h. The reaction medium is diluted with ethyl acetate, washed with water and dried over dry sodium sulphate.

The organic phase is treated with hydrochloric isopropanol and the precipitate is purified by crystallization from isopropanol to give 17 g of a pale pink powder.

Yield: 70%;

m.p.$_{(inst)}$Kofler: 143° C.;

NMR 200 MHz-TF-$^1$H (CD$_3$OD): 7.3–8.1 (m, 3H, thienyl-H); 4.3 (m, 1H, 3-piperidyl-H); 1.6–3.7 (m, 16H, CH$_2$).

c) Preparation of (4S,3'R) (−)-N-[4-(2-thienoyl)-butyl]piperid-3'-yl 2,6-dimethyl-4-(3-nitrophenyl)-5-methoxycarbonyl-1,4-dihydropyridine-3-carboxylate A suspension of 16.6 g (0.050 mol) of (4R)(−)-5-methoxycarbonyl-2,6-dimethyl-4-(3-nitrophenyl)-1,4-dihydropyridine-3-carboxylic acid, 13.4 g (0.050 mol) of the product obtained in b), 3.05 g (0.025 mol) of dimethylaminopyridine and 20.6 g (0.100 mol) of dicyclohexylcarbodiimide in 400 ml of toluene is stirred for 3 days at room temperature. The insoluble material is removed by filtration, the solvent is evaporated off and the residue is taken up in methylene chloride and successively washed with 2N sodium hydroxide solution, 2N hydrochloric acid solution and 5% potassium bicarbonate solution. The organic phase is dried over dry sodium sulphate and the solvent is evaporated off under reduced pressure.

The residue is purified by passing it through 200 g of silica (flash chromatography), eluting with a 95-methylene chloride/5-isopropanol mixture to give 18.6 g of an amorphous yellow powder.

Yield: 64%;

[α]$_D$-23 (c=1.284, MeOH);

NMR 200 MHz-TF-$^1$H (CDCl$_3$): 7.1–8.15 (m, 7H, aromatic-H); 5.1 (s, 1H, 4-dihydropyridyl-H); 4.75 (m, 1H, 3-piperidyl-H); 3.65 (s, 3H, COOCH$_3$);1.2–3 (m, 16H, CH$_2$—), 2.3 (s, 1H, NH)

EXAMPLE 2

Preparation of (4S,3'R)(−)N-[4-(2,4,6-trimethoxybenzoyl)butyl]pyrrolidin-3'-yl 2,6-dimethyl-4-(3-nitrophenyl)-5-methoxycarbonyl-1,4-dihydropyridine-3-carboxylate (CRL 42290)

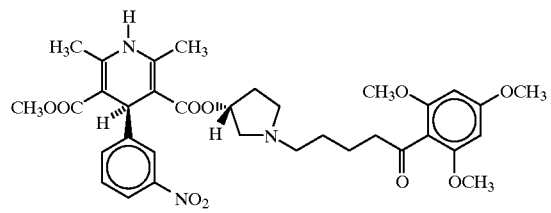

a) Preparation of 1-(2,4,6-trimethoxybenzoyl)-4-chlorobutane

A solution of 91 g (0.384 mol) of tin tetrachloride in 112.5 ml of benzene is added over 1 h 30 min to a solution, maintained at about +5° C., of 50.4 g (0.3200 mol) of 1,3,5-trimethoxybenzene and 50.2 g (0.324 mol) of 5-chlorovaleryl chloride in 225 ml of benzene. The mixture is stirred overnight at room temperature and the reaction medium is poured into 325 ml of ice-cold water and 75 ml of 12N hydrochloric acid. The organic phase is separated out after settling has taken place, washed with water and dried over dry sodium sulphate.

The oily residue is purified by washing with hexane to give 84 g of a white powder.

m.p. <50° C.;

Yield: 97.7%;

NMR 200 MHz-TF-$^1$H (CDCl$_3$): 6.1 (s, 2H, aromatic-H); 3.9 (s, 3H, methoxy-H); 3.7 (s, 6H, methoxy-H); 3.5 (t, 2H, CH$_2$Cl); 2.7 (t, 2H, CH$_2$CO); 1.8 (m, 4H, CH$_2$).

b) Preparation of (R)(−)-1-(2,4,6-trimethoxybenzoyl)-4-(3-hydroxypyrrolidino)butane hydrochloride A solution of 28 g (0.0977 mol) of the product obtained in a) in 55 ml of toluene is added, over 1 h 15 min, to a refluxing solution of 17 g (0.1955 mol) of (R)-3-hydroxypyrrolidone in 20 ml of toluene, the reaction medium is maintained at reflux for 30 min and is diluted with ethyl acetate. The mixture is washed with water and extracted with dilute hydrochloric acid solution, and the aqueous phase is basified with concentrated sodium hydroxide and re-extracted with ethyl acetate.

After drying the organic phase over dry sodium sulphate, it is treated with hydrochloric isopropanol.

The precipitate obtained is purified by crystallization from isopropanol to give 15.2 g of a slightly mauve, water-soluble powder.

m.p.$_{(inst)}$Kofler: 125° C.;

Yield=41.65%;

NMR 200 MHz-TF-$^1$H (CD$_3$OD): 6.2 (s, 2H, aromatic-H) 3.85 (s, 3H, methoxy-H), 3.75 (s, 6H, methoxy-H); 3–3.5 (m, 6H, N—CH$_2$); 2.8 (t, 2H, CH$_2$—CO); 1.6–2.1 (m, 6H, CH$_2$).

EXAMPLE 3

Preparation of (4S,3'R)(−)N-[5-(1H-pyrrol-2-yl)-5-oxopentyl]piperid-3'-yl 2,6-dimethyl-4-(3-nitrophenyl)-5-methoxycarbonyl-1,4-dihydropyridine-3-caroxylate (CRL 42547)

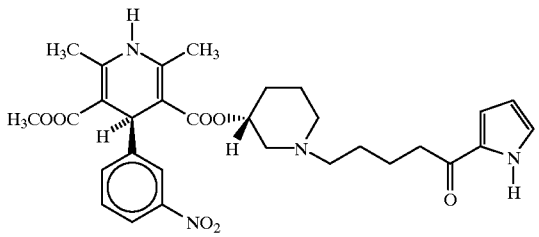

a) Preparation of 2-(5-chloropentanoyl)-1H-pyrrole

A solution of 26.7 g (0.200 mol) of aluminium chloride and 31 g (0.200 mol) of 5-chlorovaleryl chloride in 200 ml of 1,2-dichloroethane is added slowly to a solution of 13.4 g (0.200 mol) of pyrrole in 250 ml of 1,2-dichloroethane. The reaction medium is stirred for 2 h at room temperature and is poured onto ice-cold hydrochloric acid. After extraction with methylene chloride, a red-brown oil is obtained.

This product is purified by flash chromatography on silica gel 60 and eluted with a 90-hexane/10-ethyl acetate mixture, to give 15 g of a slightly orange-coloured oil.

Yield=40.4%;

NMR 200 MHz-TF-$^1$H (CDCl$_3$): 6.2–7.1 (m, 3H, pyrrole-H); 3.5 (t, 2H, CH$_2$Cl); 2.8 (t, 2H, CH$_2$—CO); 1.8 (m, 4H, CH$_2$).

c) Preparation of (4S,3'R)(−)N-[4-(2,4,6-trimethoxybenzoyl)butyl]pyrrolidin-3'-yl 2,6-dimethyl-4-(3-nitrophenyl)-5-methoxycarbonyl-1,4-dihydropyridine-3-carboxylate A solution of 9.9 g (0.048 mol) of dicyclohexylcarbodiimide in 60 ml of toluene is added to a suspension of 8 g (0.024 mol) of (4R)-5-methoxycarbonyl-2,6-dimethyl-4-(3-nitrophenyl)-1,4-dihydropyridine-3-carboxylic acid and 8.1 g (0.024 mol) of the product obtained in b) in base form, in the presence of 1.5 g (0.012 mol) of dimethylaminopyridine in 140 ml of toluene. The mixture is stirred for 4 days at room temperature, the precipitate is removed by filtration and the solvent is evaporated off under reduced pressure. The residue is taken up in chloroform and washed with 2N sodium hydroxide, 2N hydrochloric acid and 5% potassium bicarbonate solution.

After drying over dry sodium sulphate and evaporation of the solvent, the residue is purified by flash chromatography on a column of silica with a 97.5-methylene chloride/2.5-isopropanol mixture, to give 8.8 g of a water-insoluble yellow foamy powder.

Yield: 56.3%;

Total yield 22.9%;

$[\alpha]_D$-1.2 (c=1.252, MeOH);

NMR 200 MHz-TF-$^1$H (CDCl$_3$): 7.2–8.1 (m, 4H, aromatic-H); 6.1 (s, 2H, aromatic-H); 5.1 (m 2H, 4-dihydropyridyl-H; 3-pyrrolidinyl-H); 3.8 (s, 3H, methoxy-H); 3.7 (s, 6H, methoxy-H); 3.6 (s, 3H, COOCH$_3$); 2.3 (s, 6H, CH$_3$), 1.4–2.9 (m, 14H, CH$_2$).

b) Preparation of 2-[5-(3-hydroxypiperidino)-pentanoyl]-1H-pyrrole hydrochloride A solution of 16.5 g (0.089 mol) of the product obtained in a) in 20 ml of acetonitrile is added, over 1 h, to a refluxing suspension of 8.9 g (0.089 mol) of (R)-3-hydroxypiperidine, 18.4 g (0.1335 mol) of potassium carbonate and 2.2 g (0.01335 mol) of potassium iodide in 18 ml of acetonitrile, and refluxing is continued overnight. The reaction medium is diluted with ethyl acetate, washed with water and extracted with 2N hydrochloric acid solution. The aqueous phase is basified with concentrated sodium hydroxide and the insoluble material is extracted with ethyl acetate. The organic phase is treated with hydrochloric isopropanol to give 20.2 g of a green-grey powder.

m.p.$_{inst}$(Kofler)=188° C.;

Yield=79.2%;

NMR 200 MHz-TF-$^1$H (CDCl$_3$): 6.2–7.1 (m, 3H, pyrrole-H); 4.3 (m, 1H, CH—OH); 3–3.5 (m, 6H, N—CH$_2$); 2.8 (t, 2H, CH$_2$—CO); 1.6–2 (m, 8H, CH$_2$)

c) Preparation of (4S,3'R)(−)N-[5-(1H-pyrrol-2-yl)-5-oxopentyl]piperid-3'yl 2,6-dimethyl-4-(3-nitrophenyl)-5-methoxycarbonyl-1,4-dihydropyridine-3-carboxylate A solution of 15.7 g (0.076 mol) of dicyclohexylcarbodiimide in 125 ml of toluene is added to a suspension, maintained under a nitrogen atmosphere, of 12.6 g (0.038 mol) of (4R)-(−)-5-methoxycarbonyl-2,6-dimethyl-4-(3-nitrophenyl)-1,4-dihydropyridine-3-carboxylic acid and 9.5 g (0.038 mol) of the product obtained in b) in base form, in the presence of 2.3 g (0.019 mol) of dimethylaminopyridine in 250 ml of toluene. The mixture is stirred for 7 days at room temperature, the precipitate is removed by filtration and the solvent is evaporated off under reduced pressure. The residue is taken up in methylene chloride and washed with 2N sodium hydroxide, 2N hydrochloric acid and 5% potassium bicarbonate solution.

After drying over dry sodium sulphate and evaporation of the solvent, the residue is purified by flash chromatography on a column of silica with a 95-methylene chloride/5-isopropanol mixture, to give 14 g of a water-insoluble yellow foamy powder.

Yield: 65.3%;

Total yield=20.9%;

$[\alpha]_D$-2.37 (c=1.332, MeOH);

NMR 200 MHz-TF-$^1$H (CDCl$_3$): 7.3–8.1 (m, 4H, aromatic-H); 6.2–7.1 (m, 3H, pyrrole-H); 5.1 (s, 1H, 4-dihydropyridinyl-H); 4.8 (m, 1H, 2-piperidyl-H); 3.6 (s, 3H, COOCH$_3$); 1.3–2.8 (m, 16H, CH$_2$), 2.3 (s, 6H, CH$_3$).

Pharmacological results demonstrating the advantageous properties of the compounds of the invention will be given below.

1) Anticalcium activity by measuring the affinity for the DHP sites of rat cardiac ventricles The affinity of the compounds for the DHP sites of cardiac ventricles is measured from a membrane preparation of the receptors, this preparation being obtained after dissecting the ventricles, homogenization and then double-centrifugation (48,000×g; 15 min., +4° C.).

These membrane preparations are placed in contact with the specific radioactive ligand (+)-[$^3$H]-PN 200-110 and the test compound, at different concentrations. The suspension is stirred for 30 minutes at a temperature of 30° C. The reaction is then stopped by filtration using a Harvester-type system. The filter is introduced into a counting flask containing scintillation liquid. The radioactivity present on each filter is then measured by counting in a β-counter with liquid scintillation.

The intensity of the binding to the membrane receptors is defined by the (molar) concentration of the test compound which is needed to displace 50% of the amount of the specific ligand (+)-[$^3$H]-PN 200-110 prebound to the DHP sites. This concentration is the IC$_{50}$ concentration.

The results, expressed as IC$_{50}$, are given in the following table:

| Compound  | IC$_{50}$          |
|-----------|--------------------|
| Example 1 | $1.5 \times 10^{-8}$ |
| Example 2 | $7.8 \times 10^{-9}$ |

2) Anticalcium activity by measuring the KCl-mediated antagonism of the contraction of isolated rat aorta The technique employed uses a ring of arterial vascular tissue taken from rat thoracic aorta and then kept alive in aerated bicarbonated Krebs buffer, and subjected to an initial tension of 2 g. The introduction of potassium chloride KCl (in a volume of 300 $\mu$l) at a concentration $5 \times 10^{-2}$ M.l$^{-1}$ into the Krebs buffer bath generates a sustained contraction whose amplitude (isometric tension) is antagonized by the addition of a solution of the test compound of increasing concentrations, each addition being made every 5 minutes. The molar concentration of the test compound which reduces by 50% the maximum contraction observed in KCl is then calculated. This concentration is the 50% inhibitory concentration (or IC$_{50}$).

The results, expressed as ICso, are given in the following table:

| Compound  | IC$_{50}$          |
|-----------|--------------------|
| Example 1 | $1.3 \times 10^{-7}$ |
| Example 3 | $1.6 \times 10^{-7}$ |

3) Hypotensive effect in conscious, spontaneously hypertensive rats

The animals receive increasing doses of compound every 90 minutes via the gastric route.

The hypotensive effect is evaluated by means of the percentage of maximum reduction of the average arterial pressure after administration of each dose.

|           | Dose mg/kg |       |       |
|-----------|------------|-------|-------|
| Compound  | 3          | +10   | +30   |
| Example 1 | 0%         | −22%  | −45%  |
| Example 3 | −12%       | −21%  | −54%  |

4) Effect on the coronary output of anaesthetized dogs

The animals receive increasing doses of compound every 30 minutes via the intravenous route. The effect on the coronary output is evaluated by means of its percentage of maximum variation after each dose.

|              | Compound  |           |           |
|--------------|-----------|-----------|-----------|
| Dose $\mu$g/kg | Example 1 | Example 2 | Example 3 |
| 5            | 12%       | +16%      | +7%       |
| +10          | +28%      | +14%      | +30%      |
| +20          | +56%      | +34%      | +59%      |
| +40          | +72%      | +78%      | +76%      |
| +80          | +81%      | +68%      | +84%      |
| +160         | +67%      | +59%      | +84%      |
| +320         | +64%      | +33%      | +59%      |

5) Therapeutic index

The therapeutic index is defined as being the ratio between the minimum arrhythmogenic dose and the dose which increases the basal coronary output by 50% (this dose is referred to hereinbelow as the "dose which is active on the coronary output").

The minimum arrhythmogenic doses were determined for each compound on anaesthetized dogs via the intravenous route and the arrhythmogenic dose/dose which is active on the coronary output ratio (therapeutic margin) was determined.

The results obtained are given below:

| Compound              | Arrhythmogenic dose/ dose which is active on the coronary output |
|-----------------------|------------------|
| Example 1             | 640/20 = 32      |
| Example 2             | 640/40 = 16      |
| Example 3             | 640/20 = 32      |
| Example A (comparative) | 640/640 = 1    |
| Example B (comparative) | 640/640 = 1    |

The comparative compounds A and B are compounds which differ, respectively, from the compounds of Examples 1 and 2 only in the length of the chain (3 carbons instead of 4 carbons between the nitrogenous heterocycle and the

group).

A subject of the present invention is also therapeutic compositions comprising, as active principle, a compound of formula I or one of the addition salts thereof with pharmaceutically acceptable acids.

The therapeutic compositions according to the invention can be administered to man or animals orally or parenterally.

They can be in the form of solid, semi-solid or liquid preparations. As examples, mention may be made of tablets, gel-capsules, suppositories, injectable suspensions or solutions, as well as delay forms and slow-release implanted forms.

In these compositions, the active principle is generally mixed with one or more common pharmaceutically acceptable excipients which are well known to those skilled in the art.

The amount of active principle administered depends, needless to say, on the patient being treated, the route of administration and the severity of the complaint.

What is claimed is:

1. Compounds of formula:

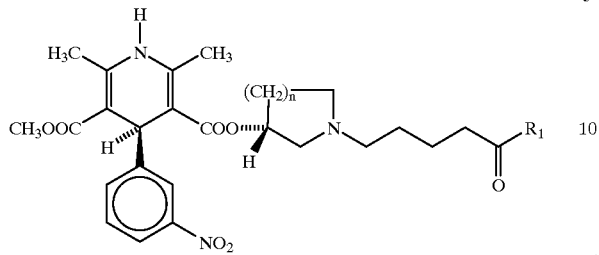

(I)

in which:

n=1 or 2, and

R₁ is a group selected from 2,4,6-trimethoxyphenyl, 2-thienyl and 2-pyrrolyl groups, and the addition salts thereof with pharmaceutically acceptable acids.

2. Compound according to claim 1, which is (4S,3'R)(−) N-[4-(2-thienoyl)butyl]piperid-3'-yl 2,6-dimethyl-4-(3-nitrophenyl)-5-methoxycarbonyl-1,4-dihydropyridine-3-carboxylate, and the addition salts thereof with pharmaceutically acceptable acids.

3. Compound according to claim 1, which is (4S,3'R)(−) N-[4-(2,4,6-trimethoxybenzoyl)butyl]pyrrolidin-3'-yl 2,6-dimethyl-4-(3-nitrophenyl)-5-methoxycarbonyl-1,4-dihydropyridine-3-carboxylate, and the addition salts thereof with pharmaceutically acceptable acids.

4. Compound according to claim 1, which is (4S,3'R)(−) N-[5-(1H-2-pyrrolyl)-5-oxopentyl]piperid-3'-yl 2,6-dimethyl-4-(3-nitrophenyl)-5-methoxycarbonyl-1,4-dihydropyridine-3-carboxylate, and the addition salts thereof with pharmaceutically acceptable acids.

5. Process for preparing a compound according to claim 1, comprising the reaction of the acid of formula:

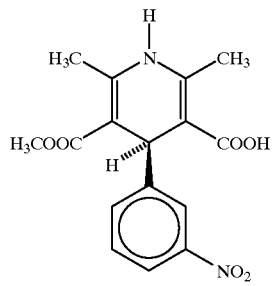

(II)

with an alcohol of formula

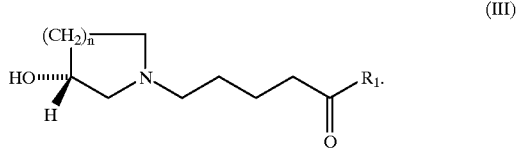

(III)

6. A pharmaceutical composition comprising an effective amount of the compound according to claim 1 in combination with a pharmaceutically acceptable carrier.

7. A pharmaceutical composition comprising an effective amount of the compound according to claim 2 in combination with a pharmaceutically acceptable carrier.

8. A pharmaceutical composition comprising an effective amount of the compound according to claim 3 in combination with a pharmaceutically acceptable carrier.

9. A pharmaceutical composition comprising an effective amount of the compound according to claim 4 in combination with a pharmaceutically acceptable carrier.

* * * * *